US009324224B2

(12) United States Patent
Schumacher

(10) Patent No.: US 9,324,224 B2
(45) Date of Patent: Apr. 26, 2016

(54) CUFFS FOR RESTRICTION OF VEHICLE OPERATION

(75) Inventor: Barry Lee Schumacher, Aspen, CO (US)

(73) Assignee: Barry Lee Schumacher, Aspen, CO (US)

( * ) Notice: Subject to any disclaimer, the term of this patent is extended or adjusted under 35 U.S.C. 154(b) by 305 days.

(21) Appl. No.: 13/198,200

(22) Filed: Aug. 4, 2011

(65) Prior Publication Data

US 2012/0032807 A1 Feb. 9, 2012

Related U.S. Application Data

(60) Provisional application No. 61/370,915, filed on Aug. 5, 2010.

(51) Int. Cl.

| | |
|---|---|
| ***G08B 23/00*** | (2006.01) |
| ***B60R 25/10*** | (2013.01) |
| ***G08B 1/08*** | (2006.01) |
| ***B60K 28/00*** | (2006.01) |
| ***G01C 9/00*** | (2006.01) |
| ***A61B 5/00*** | (2006.01) |
| ***G08B 21/04*** | (2006.01) |

(52) U.S. Cl.
CPC ........ *G08B 21/0446* (2013.01); *G08B 21/0453* (2013.01)

(58) Field of Classification Search
CPC ........................................................ G08B 23/00
USPC ........................................................ 340/573.1
See application file for complete search history.

(56) References Cited

U.S. PATENT DOCUMENTS

| | | | | |
|---|---|---|---|---|
| 5,902,189 | A * | 5/1999 | Schultz | 473/212 |
| 6,075,444 | A | 6/2000 | Sohege et al. | |
| 6,762,687 | B2 * | 7/2004 | Perlman | 340/573.1 |
| 2002/0198472 | A1 | 12/2002 | Kramer | |

(Continued)

FOREIGN PATENT DOCUMENTS

| | | | |
|---|---|---|---|
| CN | 86205971 | U | 7/1987 |
| CN | 201078753 | Y | 6/2008 |
| KR | 2004098608 | A | 11/2004 |

OTHER PUBLICATIONS

International Search Report and Written Opinion, PCT/US2011/046626, dated Dec. 8, 2011, 10 pages.

*Primary Examiner* — Fekadeselassie Girma
*Assistant Examiner* — John Mortell
(74) *Attorney, Agent, or Firm* — Polsinelli PC

(57) ABSTRACT

Operation of a generally requires that the operator have sufficient range of motion in the upper limbs to 1) steer the vehicle and/or 2) to operate the vehicle's ancillary controls. The presently disclosed technology provides for limiting upper limb movement by requiring a user's upper limbs to be oriented in a way as to limit or prevent the user from being able to operate the vehicle. Cuffs may be secured to a variety of locations on a user's upper limbs. In a predetermined upper limb position, the cuffs are oriented in a specific location and orientation on the user's upper limbs and in a specific proximity and orientation with respect to one another. The user is compliant by maintaining the cuffs in the predetermined upper limb position. To ensure compliance, the cuffs are equipped with a compliance monitor that monitors the cuffs contact, proximity, and/or orientation with one another in conjunction with GPS information such as location and/or speed.

22 Claims, 9 Drawing Sheets

(56) References Cited

U.S. PATENT DOCUMENTS

| | | | |
|---|---|---|---|
| 2004/0236199 | A1 | 11/2004 | Hawthorne et al. |
| 2005/0193782 | A1 | 9/2005 | Beane et al. |
| 2008/0174451 | A1 | 7/2008 | Harrington et al. |
| 2008/0183388 | A1 | 7/2008 | Goodrich |
| 2009/0260638 | A1 | 10/2009 | Duplessie |
| 2011/0054833 | A1* | 3/2011 | Mucignat ...................... 702/150 |
| 2011/0156912 | A1* | 6/2011 | Lin et al. .................... 340/573.1 |
| 2011/0199256 | A1* | 8/2011 | Chu ......................... 342/357.25 |

* cited by examiner

CUFFS FOR RESTRICTION OF VEHICLE OPERATION

CROSS-REFERENCE TO RELATED APPLICATIONS

The present application claims benefit of priority to U.S. Provisional Patent Application No. 61/370,915, entitled "Cuffs for Restriction of Vehicle Operation" and filed on 5 Aug. 2010, which is specifically incorporated by reference herein for all that it discloses or teaches.

BACKGROUND

Drunk drivers typically have a high rate of recidivism. Several schools of thought exist as to the "best" method of addressing those convicted of driving under the influence (DUI) or driving while intoxicated (DWI). Some courts focus on rehabilitation of offenders, while others focus on punishing the driver by revoking or restricting driving privileges or assessing fines.

Some offenders, for example, are required to install an ignition interlock device (IID) in his or her personal vehicle before revoked driving privileges are restored. IIDs, such as breathalyzer ignition locks, require that the driver blow a breath sample into the IID before starting the vehicle. If the breath sample exceeds a pre-set, "acceptable" alcohol content, the vehicle will not start. However, nothing prevents the driver from having another party blow into the IID for them. Further, nothing prevents an offender from driving another vehicle that does not have an IID installed.

While incarceration is an effective tool to remove recidivist offenders from the road, it is rarely imposed because drunk drivers tend not to be perceived as "bad" people until they kill or injure someone else. Further, incarceration is expensive and the high cost is often passed on to taxpayers. Still further, incarceration is only a temporary fix—it does nothing to stop one from operating a motor vehicle once released from incarceration.

SUMMARY

The presently disclosed technology provides for an apparatus and system to limit or prevent the operation of a vehicle by an individual that has had his/her driving privileges restricted or revoked. This presently disclosed technology is configured to be worn by a user and, thus, is not specific to any type vehicle and may be applied to motorized vehicles and non-motorized vehicles. Further, the presently disclosed technology is configurable to permit operation of a vehicle during specified hours, or the operation of a vehicle above or below specified speeds. A benefit of the presently disclosed technology is to effectively prevent a person who has lost driving privileges from operating a moving vehicle, while allowing the same person to be a passenger in that or any other moving vehicle.

BRIEF DESCRIPTIONS OF THE DRAWINGS

DETAILED DESCRIPTIONS

Operation of a vehicle (e.g., a car, truck, bicycle, scooter, motorcycle, boat, aircraft, etc.) generally requires that the operator have sufficient range of motion in the upper limbs to 1) steer the vehicle and/or 2) to operate the vehicle ancillary controls (e.g., a gearshift). The presently disclosed technology provides for limiting upper limb movement by requiring a user's upper limbs to be oriented in a way as to limit or prevent the user from being able to steer a vehicle.

Figure 1:
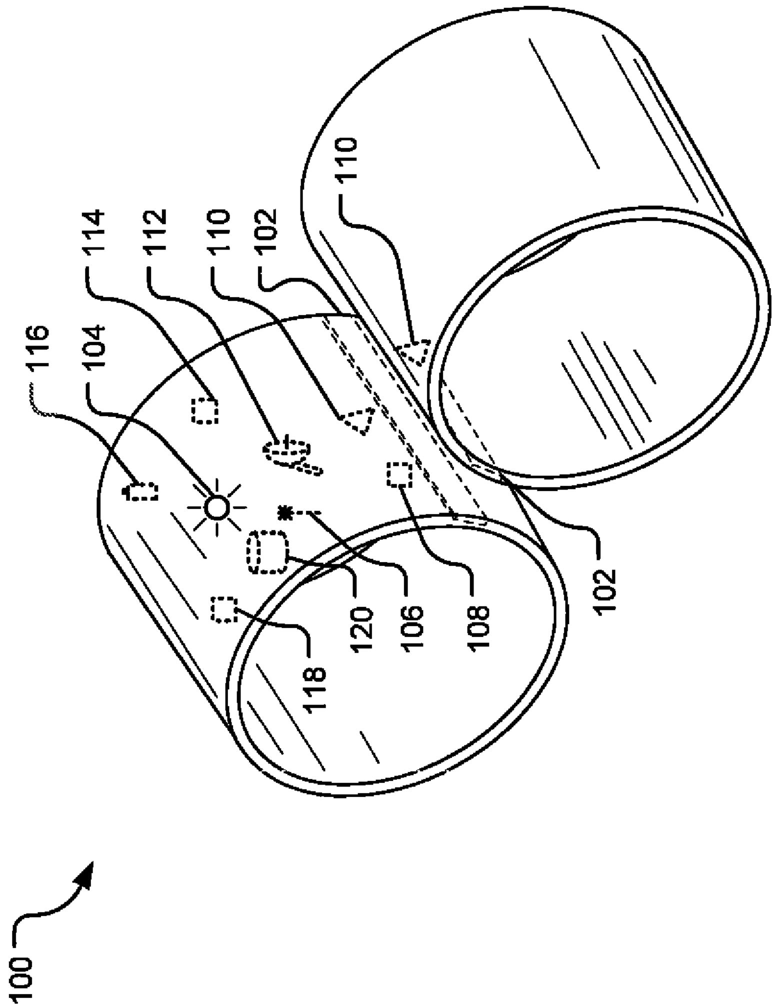
FIG. 1 illustrates an example pair of position monitoring upper limb cuffs according to the presently disclosed technology.

FIG. 1 illustrates an example pair of position monitoring upper limb cuffs 100 according to the presently disclosed technology. The cuffs 100 may be secured to a variety of locations on a user's upper limbs (e.g., the user's wrists or forearms as in FIG. 4, the user's arms as in FIG. 7, and the user's shoulders). In a predetermined upper limb position, the cuffs 100 are oriented in a specific location and orientation on the user's upper limbs and in a specific proximity and orientation with respect to one another (see e.g., FIG. 4). The user is compliant by maintaining the cuffs 100 in a predetermined upper limb position. In non-compliant positions, the cuffs are not oriented in a position that satisfies all the requirements of the predetermined upper limb position. The user is non-compliant when he/she fails to maintain the cuffs 100 in a predetermined upper limb position.

To ensure compliance, the cuffs 100 are equipped with a compliance monitor 102 that monitors the cuffs 100 contact, proximity, and/or orientation with one another. The compliance monitor 102 may also monitor position and/or orientation of the cuffs 100 on each of the user's upper limbs. The cuffs 100 may include one or more proximity, contact, or orientation sensors within the compliance monitor 102 to ensure compliance. The compliance monitor 102 may still further monitor whether the user's hands and/or wrists are in contact or close proximity to the cuff on the user's opposite upper limbs. The net result is that the compliance monitor 102 monitors whether the user's upper limbs are in a position in which the user cannot reasonably operate a vehicle.

In one implementation, the opposing compliance monitors 102 are in close proximity (e.g., less than 0.5 inches) from one another and oriented in opposite directions (e.g., within 5 degrees of 180 degrees from one another) to ensure compliance. If the cuffs 100 exceed 0.5 inches from one another and/or become oriented outside of 175-185 degrees from one another, the user is non-compliant.

In another implementation, the compliance monitors 102 permits the cuffs 100 to be in close proximity or electronic or mechanical contact with each other (or another electronic or mechanical device) and in a position that prohibits operation of a motor vehicle and 2) engages a proximity, mechanical, or electronic compliance indicator 104 switch (discussed in detail below).

In yet another implementation, the compliance monitors 102 may include an electromagnetic sensor that is engagable through clothing, and requires the monitors 102 to be placed in proximity to each other but in opposite orientations, placing the upper limbs of the user in a position such that each of the user's palm is oriented towards the opposite palm. In some implementations, this electronic position fixation mechanism may be speed-sensitive, such that it will not engage below a pre-defined speed, and it will disengage when the user's speed drops below a pre-defined speed. In an implementation, engaging the compliance monitors 102 may also engage a switch that provides feedback transmitted via a transmitter (see e.g., transmitter 106, discussed in detail below) to a monitoring center, indicating that the electronic position fixation mechanism is engaged.

A compliance indicator 104 notifies the user if the user is non-compliant with the predetermined upper limb position. To notify the user, the compliance indicator 104 may include one or more visual (e.g., flashing or steady light(s)), auditory (e.g., a steady or varying tone emitted from a speaker), or tactile (e.g., vibration or electric shock) feedback when the user becomes non-compliant. The user may then return the cuffs 100 to the predetermined upper limb orientation to cease the visual, auditory, and/or tactile feedback.

In other implementations, the compliance indicator 104 may be adapted to provide an auditory signal, such as a beep or chirp, when the cuffs 100 are oriented in a predetermined upper limb position. In other implementations, the compliance indicator 104 may include different visual or auditory indicators that signal the user that sufficient speed has been attainted to require putting the cuffs 100 in the predetermined upper limb position.

The cuffs 100 may further include a GPS (global positioning system) or other geolocation locator 114 that tracks the user's movements, including speed. In one example implementation, the cuffs 100 only become active (i.e., requiring the user's compliance) when the user is moving at a speed exceeding a threshold or lies within a range. For example, if the user is prohibited from driving an automobile, but is permitted to bicycle, the cuffs 100 may only be active when the user is moving at a rate exceeding 15 miles an hour. In an implementation where the user is prohibited from bicycling and driving a car, the cuffs 100 may only be active when the user is moving at a rate exceeding 8 miles an hour. The cuffs 100 may also become inactive when the user's speed exceeds that reasonably achievable in an automobile (e.g., 150 miles and hour) to facilitate the user's travel aboard commercial aircraft. The specific speed thresholds may be adjustable by an authorized party (e.g., in compliance with a court order).

A monitoring agency may contact law enforcement (if the monitoring agency is not law enforcement itself), either in the user's "home" area or a law enforcement agency near the last known GPS coordinates of the cuffs 100 if violations occur. The locator 114 may also be used to track geographic restrictions on the user. In one implementation, terms of the user's probation may limit his travels to a pre-specified distance from the user's home and/or workplace or confine the user to the user's home. As such, the locator 114 can track whether the user is complying with the user's geographic restrictions. In another implementation, if the user is fleeing from authorities, the locator 114 may be used as a tracking device to help the authorities locate the user in hiding. Further, the cuffs 100 could emit a loud noise, also to help the authorities locate the user in hiding. The presently disclosed technology may be used to enforce sentencing requirements imposed by criminal courts, or as a behavior modification tool.

The cuffs 100 may further include a compliance transmitter 106 that transmits to monitoring authorities the user's compliance or non-compliance. For example, the compliance transmitter 106 may transmit a signal when the user become non-compliant and fails to return the cuffs 100 to the predetermined upper limb orientation within a specified period of time (e.g., 10 seconds) and maintain the cuffs 100 in the predetermined upper limb orientation for a minimum period of time (e.g., 5 minutes) before becoming non-compliant again. The compliance transmitter 106 may further notify authorities when the user has traveled beyond the user's geographic restrictions imposed by a probation sentence. The compliance transmitter 106 may operate over radio, cellular, GPS, or other networks to communicate the user's activities, including the user's location, velocity, compliance or non-compliance, etc. to monitoring authorities.

In one implementation, the user's upper limbs may be released under certain conditions and re-constrained when the conditions change. For example, when the vehicle is moving, the cuffs 100 are engaged to prevent an alert from triggering. However, the user in a front passenger seat may elect to temporarily disengage or separate cuffs 100 to reach the back seat of the vehicle, for example. The user may then re-engage the cuffs 100 within a fixed timeframe (e.g., 60 seconds) to prevent the alert from triggering. Alternatively, the cuffs 100 may be configured with an electronic locking mechanism that cannot be disengaged or separated while the vehicle is moving at a speed in excess of a threshold (e.g., 15 mph). The device may be plastic that could be broken by the user in an emergency or metal if the user should not be able to break the device.

In another implementation, the cuffs 100 utilize a constant connection with the monitoring authorities via the compliance transmitter 106. When that connection is broken, the authorities are notified and perhaps dispatched to find the user if the connection is not reestablished within a predetermined timeframe. Further, a warrant may be issued for the user's arrest if the connection is not reestablished within a predetermined timeframe. Still further, the locator 114 may be used to excuse the loss of connection to the monitoring authorities due to geographic limitations. For example, if the locator 114 indicates that the user was near or within a tunnel, near or within very tall buildings, or within a very mountainous area, loss of the constant connection may be excused if reestablished within a longer predetermined timeframe than if the constant connection is lost for no apparent reason.

In another implementation, the cuffs 100 may be monitored via the user's Smartphone or other portable computing device. For example, the user may pair the cuffs 100 with his/her Smartphone (via e.g., Bluetooth technology) and download a tracking application for the Smartphone or other portable computing device. If a connection with monitoring authorities is lost, the Smartphone or other computing device may store monitoring data from the cuffs 100 until a connection with the monitoring authorities is restored. When the connection with the monitoring authorities is restored, the data stored in the Smartphone regarding the user's compliance may be uploaded to the monitoring authorities.

The transmitter 106 may be configured to transmit in any fashion that can be monitored by a monitoring center. In one implementation, the transmitter 106 may be configured to transmit position information on a specified monitored radio frequency, in a fashion similar to an emergency position-indicating radio beacon (EPIRB), emergency locator transmitter (ELT), or personal locator beacon (PLB). In another implementation, the transmitter 106 may be similar to a cellular phone, and may transmit data to the monitoring center via any of a variety of protocols, such as short message service (SMS) or other data service. A cellular phone-type transmitter 106 may be further configured to directly contact an emergency number (e.g., 911) or a specified law enforcement agency when a violation occurs. A satellite-type transmitter 106 may also be used. Further, in some implementations, the transmitter 106 may serve as a geolocation device and may be used to determine approximate speed.

In some implementations, multiple types of transmitters 106 are combined in the cuffs 100 to provide redundancy in case one connection is broken, yet another connection is still active. For example, in particularly stormy weather conditions, a satellite-based connection may be lost while a ground-based radio connection may be maintained. Still further, certain locations may be unavailable for a connection to the cuffs 100. For example, various large tunnels, parking garages or the like may be excluded from coverage. Either the user may be prohibited from those areas as a part of his/her parole or the locator 114 will detect that the cuffs 100 are approaching those areas and excuse any loss of signal as caused by location rather than the user's failure to orient the cuffs in a predetermined upper limb position.

The transmissions of the transmitter 106 are configurable. For example, the transmitter may be configured to transmit only when a pre-defined speed is exceeded, during specific hours, randomly, or only when a violation (such as unauthorized removal of a cuff or exceeding a pre-defined speed without engaging the switch indicating compliance) occurs. Further, the transmitter 106 may be activated remotely by the monitoring center or law enforcement. Still further, the transmitter 106 may also transmit in the event of an accident, for example, if it experiences an abrupt deceleration and lack of further movement.

The cuffs 100 may further include a receiver 112 that receives information from monitoring authorities regarding the user's compliance or non-compliance. For example, if the monitoring authorities are searching for the user, the cuffs 100 may emit a strong light or sound via indicator 104 to aid the monitoring authorities in locating the user. The monitoring authorities may also remotely activate or deactivate the cuffs 100 via the receiver 112.

The cuffs 100 may further include a biomonitor 108 that monitors one or more of the user's vital signs and other readings (e.g., the user's temperature, pulse, blood pressure, blood-alcohol level, etc.). The biomonitor 108 may be used to ensure that the cuffs 100 are correctly oriented (e.g., positioned over the user's wrists for a strong pulse reading). The biomonitor 108 may also be used to ensure that the user has not removed one or both of the cuffs 100 (the user's vital signs would be zero on that cuff) and that the cuffs 100 have not be tampered with or damaged. The biomonitor 108 may further still have an alcohol sensor that may be used to ensure that the user is not intoxicated (e.g., via continuous transdermal alcohol monitoring).

In this implementation, if the user passes an alcohol test using the alcohol sensor, the cuffs 100 may be unlocked where compliance is not required and the user permitted to operate a vehicle. The alcohol sensor may be configured to require compliance with the predetermined upper arm position if the user has any alcohol in the user's system or if the alcohol in the user's system exceeds a predefined threshold.

In another implementation, the cuffs 100 may indicate to the user when an alcohol test using the alcohol sensor is required. For example, an alcohol test may be required at predetermined intervals or when the cuffs 100 exceed a pre-defined speed.

The cuffs 100 may further include a physical latching mechanism 110 to aid the user in compliance. The latching mechanism 110 may have corresponding male and female components on each cuff. When interlocked, the male and female components aid the user in maintaining the cuffs 100 in a compliant orientation. For example, the interlocked connection is strong enough to prevent the user from inadvertently moving the cuffs 100 into a non-compliant position, but weak enough to enable the user to beak the connection in an emergency. In another implementation, the latching mechanism 110 is strong enough to prevent the user from breaking the connection, even intentionally. The cuffs 100 may include an override button to release the connection in an emergency. The latching mechanism 110 may work in conjunction with the compliance monitor 102 in that the cuffs 100 are only in compliance whether the latching mechanism 110 physically secures the cuffs 100 together.

Figure 4:
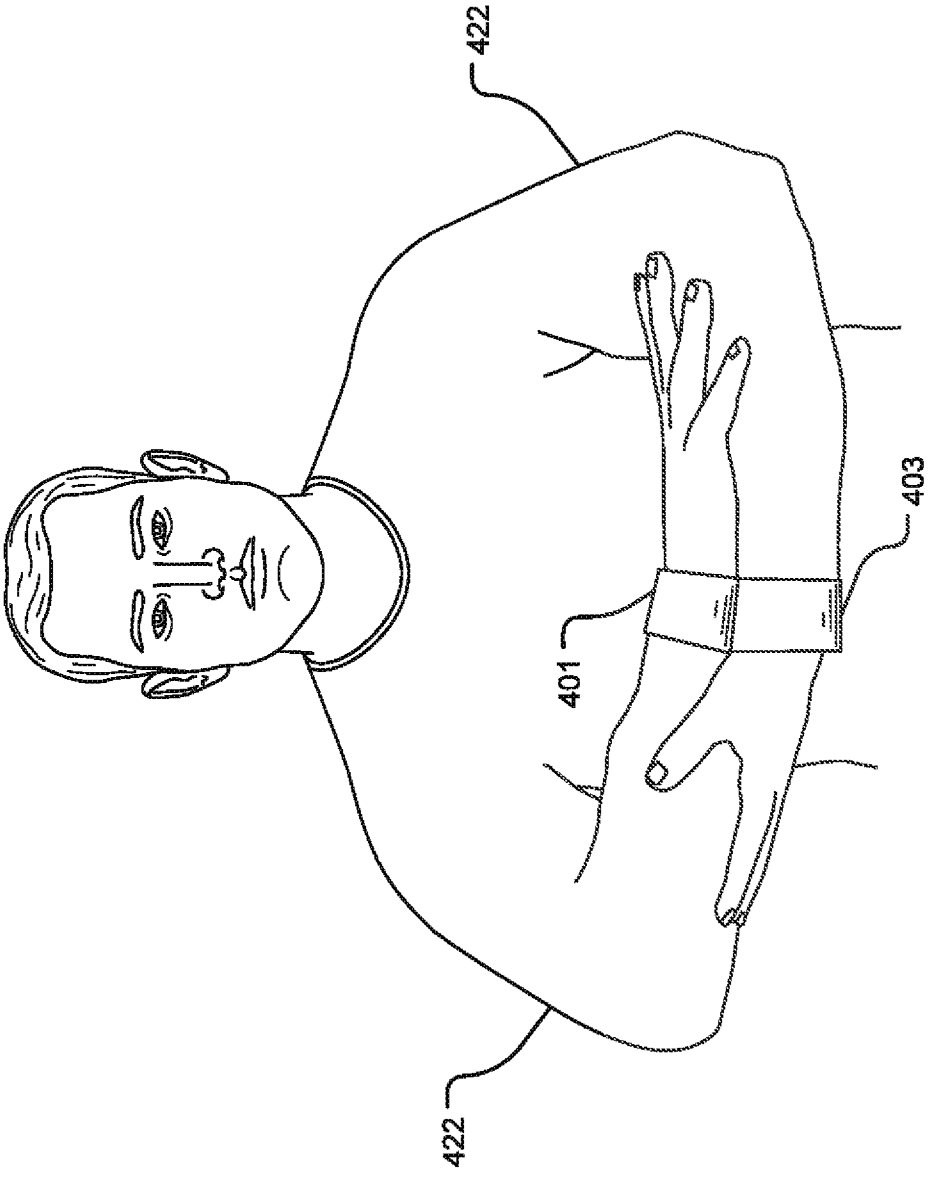
FIG. 4 illustrates a user's upper limbs, each equipped with an example position monitoring forearm cuff, oriented in a predetermined upper limb position.

In the depicted implementation, the latching mechanism 110 is a triangular-shaped protrusion of each of the cuffs 100, wherein one of the protrusions is configured to lock inside the other protrusion when the cuffs 100 are locked together (e.g., in a male-female connection). The triangular-shaped protrusions point opposite directions so that they are configured to interface with one another when the user places his/her arms in a locked position as depicted in FIG. 4. Other shaped protrusions are also contemplated herein. In one implementation, only one of the cuffs 100 is equipped with a protrusion. The opposite cuff is equipped with a matching recess configured to accept the protrusion when the cuffs 100 are in a locked position.

In one implementation, when the cuffs 100 are in a locked position, each of the user's hands wrap around the user's opposite forearm near the user's elbow with the user's inside wrists facing one another. In another implementation, the cuffs 100 are positioned so that each of the user's hands touch or wrap around the user's opposite elbow. In some implementations, the positions of the protrusions on the cuffs 100 are adjustable for a variety of arm sizes. In other implementations, the cuffs 100 themselves are adjustable instead of or in addition to the protrusions. In one implementation, each of the points of one of the triangular protrusions has sensors and/or alignment protrusions that interface with the points of the opposite triangular protrusion and indicates that the cuffs 100 are completely aligned when locked together.

In another implementation, a first cuff may include a tab that is adapted to engage with a slot on a second cuff (together a latching mechanism 110) when the user's forearms are oriented such that the user's palms are facing one another (i.e., a predetermined upper limb position). When the user rotates his or her forearms, the latching mechanism 110 may engage to fix the user's forearms in the predetermined upper limb position. In some implementations, the latching mechanism 110 may be speed-sensitive, such that it will not engage below a pre-defined speed, and it will disengage when the user's speed (determined by the locator 114) drops below a pre-defined speed. This would permit the latching mechanism 110 to disengage, for example, in the event of a motor vehicle accident. In an implementation, engaging the latching mechanism 110 may also engage a switch that provides feedback transmitted via a transmitter to the monitoring center via the transmitter 106, indicating that the latching mechanism 110 is engaged. In many implementations, the latching mechanism

110 is unnecessary because a transmission of a notice of a violation to the monitoring center via the transmitter 106 is a sufficient deterrent preventing the user from disengaging the latching mechanism 110 when it is required to be engaged. An easily engaged and disengaged clasp, snap or other selective attachment may be used to provide tangible feedback to the user that the cuffs 100 are in a predetermined upper limb position.

The cuffs 100 may further include data storage 120 capable of storing collected information regarding the user's position, speed, and cuff engagement data, reducing the need for real-time monitoring. This data may be downloadable by a monitoring center or law enforcement to determine compliance over time.

The cuffs 100 may further include one or more batteries 116 to power the various components and functions of the cuffs 100. The battery 116 may be incorporated into the cuffs 100 themselves (as shown in FIG. 1) or separate from the cuffs (not shown), but electrically connected to the cuffs 100 (e.g., via one or more wires). Further, the battery 116 may incorporate any electrical power storage technology (e.g., lithium-ion, nickel-cadmium, alkaline, etc.) or alternative power source such as a micro fuel cell. Still further, the battery 116 may be replaceable, rechargeable, or both. If rechargeable, the battery 116 may be recharged via connection to the electricity grid, solar panel, mechanical winding, etc.

In an implementation, the cuffs 100 may include other electronics 118 that form a complete circuit when the cuffs 100 are engaged. Accordingly, unauthorized removal of either cuff would result in the circuit being broken and may result in an alarm condition that is transmitted to the monitoring center via transmitter 106 to indicate that a violation has occurred. Still further, the cuffs 100 may include various tamper-protection technologies to prevent the user from circumventing the electronics 118 that form a complete circuit or any other features of the cuffs 100. In another implementation, the cuffs 100 may permit the user to remove them for a specified period of time (e.g., time to take a shower) before re-attaching the cuffs 100.

The cuffs 100 may each be made of rigid materials (e.g., plastics, metals, wood), flexible materials (rubber, fabrics (natural and/or synthetic)), or any combination thereof. Further, the cuffs 100 may be decorative (e.g., jewelry-like) or similar in appearance to a watch band or bracelet. Still further, the cost of the cuffs 100 and/or monitoring services may be borne by the user, so that the taxpayer is not burdened with the costs. Further, the cost to the user may exceed the actual cost of the cuffs 100 and/or monitoring services. In this implementation, the presently disclosed technology can actually generate revenue. The monitoring service described herein may be provided as subscription services.

Figure 2:
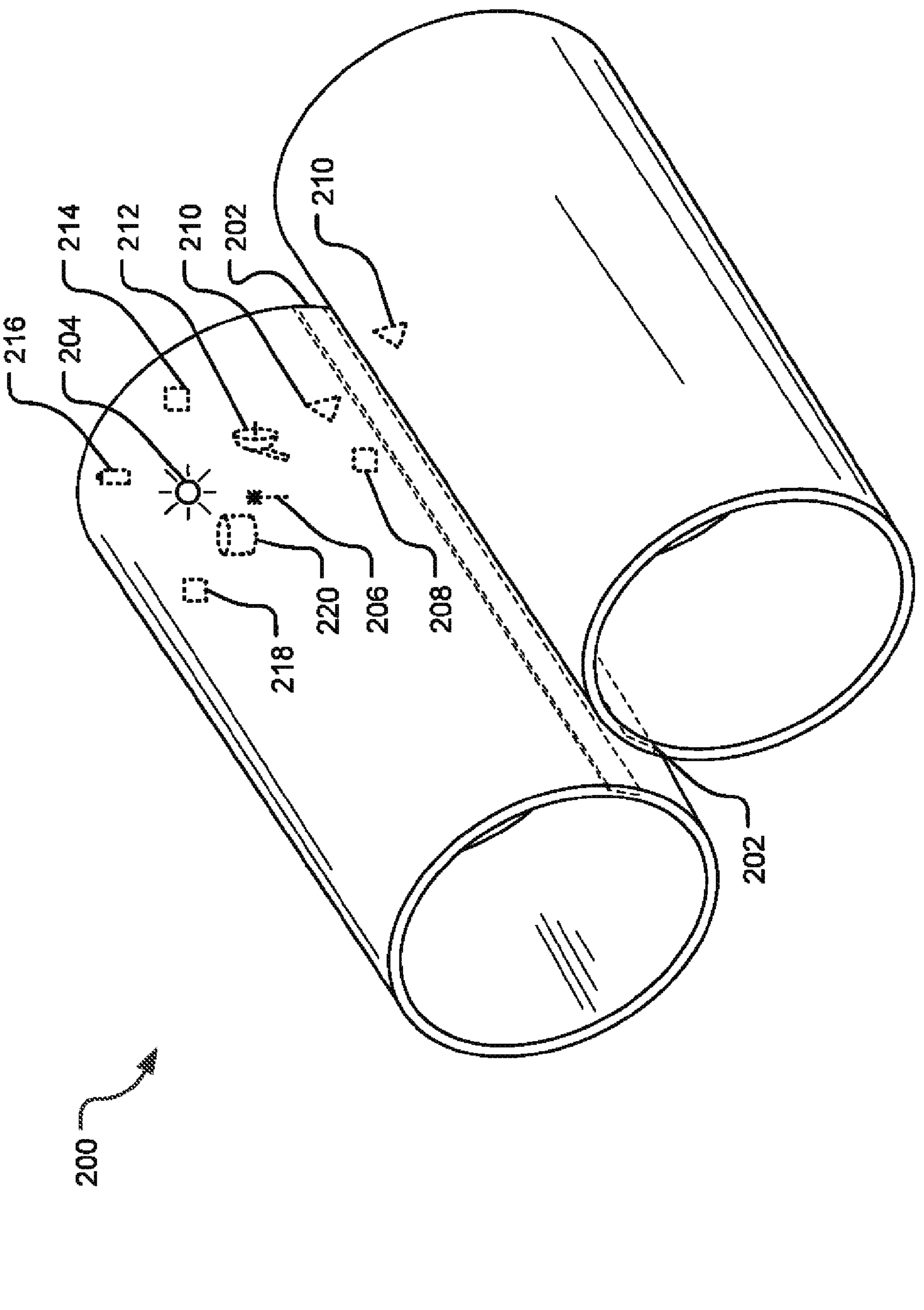
FIG. 2 illustrates an example pair of position monitoring forearm gauntlets according to the presently disclosed technology.

FIG. 2 illustrates an example pair of position monitoring forearm gauntlets 200 according to the presently disclosed technology. The gauntlets 200 may encompass and be secured to a user's forearms. In a predetermined upper limb position, the gauntlets 200 are oriented in a specific location and orientation on the user's forearms and in a specific proximity and orientation with respect to one another (see e.g., FIG. 5). The user is compliant by maintaining the gauntlets 200 in the predetermined upper limb position. In non-compliant, the gauntlets 200 are not oriented in a position that satisfies all the requirements of the predetermined upper limb position. The user is non-compliant when he/she fails to maintain the gauntlets 200 in the predetermined upper limb position.

The gauntlets 200 may include one or more of a compliance monitor 202, compliance indicator 204, transmitter 206, biomonitor 208, latching mechanism 210, receiver 212, locator 214, battery or other power source 216, data storage 220, and other electronics 218. The various functions of the components 202, 204, 206, 208, 210, 212, 214, 216, 218, 220 are as described above with regard to components 102, 104, 106, 108, 110, 112, 114, 116, 118, 120 of FIG. 1.

Figure 3:
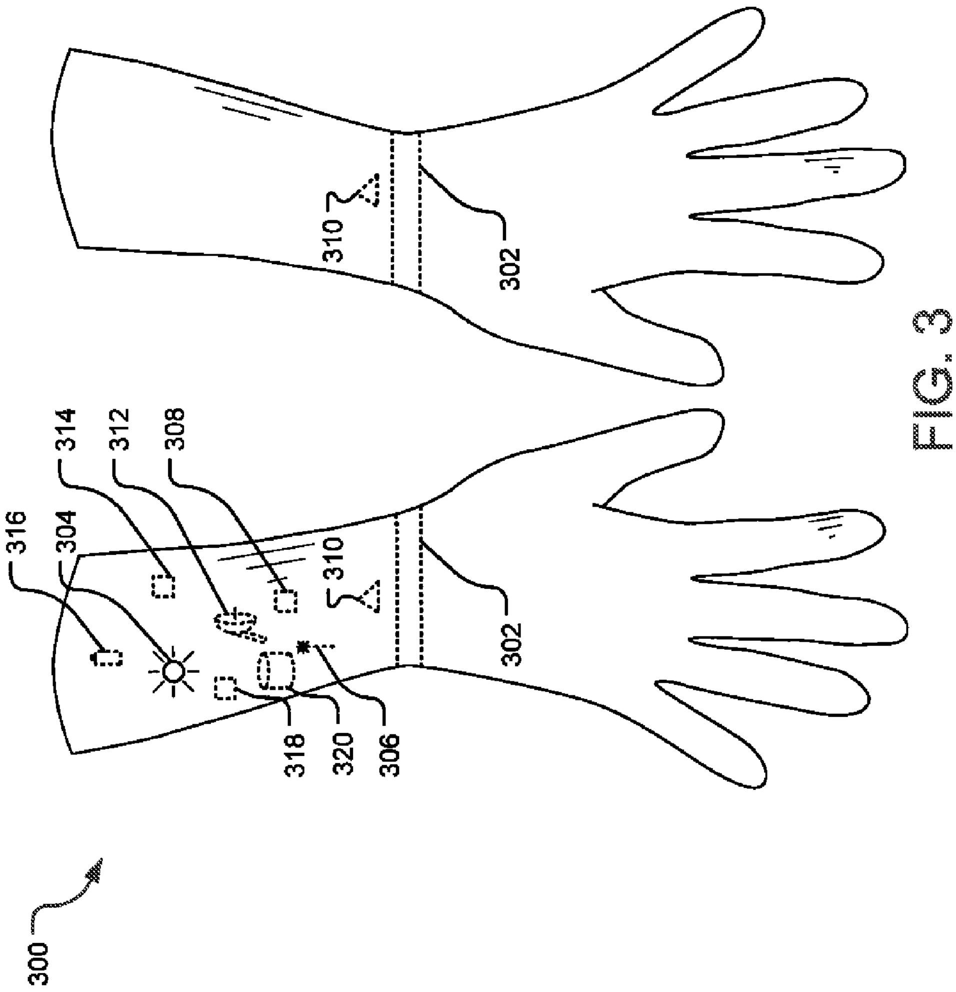
FIG. 3 illustrates an example pair of position monitoring fingered forearm gauntlets according to the presently disclosed technology.

FIG. 3 illustrates an example pair of position monitoring fingered forearm gauntlets 300 according to the presently disclosed technology. The gauntlets 300 may encompass and be secured to at least a portion of a user's forearms, wrists, hands, and fingers. In a predetermined upper limb position, the gauntlets 300 are in a specific proximity and orientation with respect to one another (see e.g., FIG. 6). The user is compliant by maintaining the gauntlets 300 in the predetermined upper limb position. In non-compliant positions, the gauntlets 300 are not oriented in a position that satisfies all the requirements of the predetermined upper limb position. The user is non-compliant when he/she fails to maintain the gauntlets 300 in the predetermined upper limb position.

In one implementation, the user's hands are not available for use at all when the gauntlets 300 are locked. This implementation is particularly effective if the user is likely to attempt to operate a vehicle anyway with his forearms locked together using the cuffs 100 of FIG. 1 or gauntlets 200 of FIG. 2. That user will have an exceedingly difficult time operating the vehicle with the gauntlets 300 locked together with user's hands encompassed.

The gauntlets 300 may include one or more of a compliance monitor 302, compliance indicator 304, transmitter 306, biomonitor 308, latching mechanism 310, receiver 312, locator 314, battery or other power source 316, data storage 320, and other electronics 318. The various functions of the components 302, 304, 306, 308, 310, 312, 314, 316, 318, 320 are as described above with regard to components 102, 104, 106, 108, 110, 112, 114, 116, 118, 120 of FIG. 1.

FIG. 4 illustrates a user's upper limbs 422, each equipped with an example position monitoring forearm cuff 401, 403, oriented in a predetermined upper limb position. The cuffs 401, 403 are each oriented on the user's forearms in the vicinity of the user's wrists. The exact position of the cuffs 401, 403 on the user's forearms may vary due to variations in the cuff and forearm size and shape. In the depicted predetermined upper limb position, the user's upper limbs 422 are oriented such that the user's wrists are adjacent one another and each of the user's palms are facing the opposing forearm. In this orientation, the user's upper limbs 422 are not effectively able to 1) steer a vehicle and/or 2) to operate the vehicle ancillary controls. The forearm cuffs 401, 403 may be equipped with a variety of features as described above with regard to FIG. 1.

In an example implementation, the cuffs 401, 403 may be oriented in an unlocked (or non-compliant) orientation and a locked (or compliant) orientation. The locked (or compliant) orientation is depicted in FIG. 4. In the unlocked orientation, the user has a cuff secured to each of the user's forearms. When placed in the locked orientation, the user places his/her forearms together with each of his/her palms facing an opposing forearm. Each of the cuffs 401, 403 may be equipped with a locking mechanism positioned on the inside of the user's forearms that is configured to interface with the opposing cuff.

In another implementation, the user's upper limbs 422 may be fixed, using electrical or mechanical means, such that the user's upper limbs 422 are fixed to the sides of the user. Still further, the user's upper limbs 422 may be fixed, using electrical or mechanical means to another point on the user (e.g., a belt or leg bands) or point(s) in the vehicle. However, it should be understood that other positions or configurations may exist to fix the user's upper limbs 422.

For example, a proximity device may be incorporated into a portion of the user's clothing (e.g., a belt) and first and second cuffs located on the user's upper limbs 422 must be in contact or close proximity to the proximity device to ensure compliance. Further, additional proximity devices may be attached to the vehicle (e.g., one on each side of the passenger seat so that the user's upper limbs 422 must remain extended down adjacent each side of the passenger seat.

Figure 5:
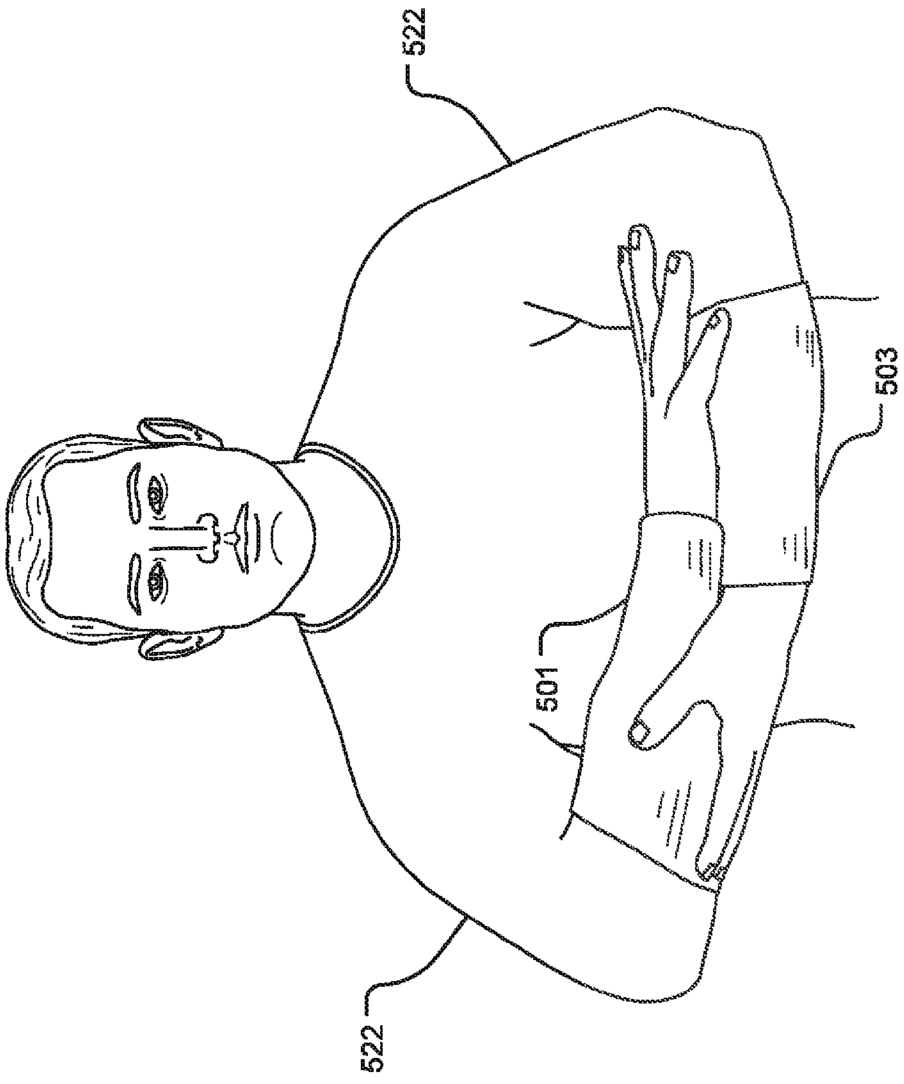
FIG. 5 illustrates a user's upper limbs, each equipped with an example position monitoring forearm gauntlet, oriented in a predetermined upper limb position.

FIG. 5 illustrates a user's upper limbs 522, each equipped with an example position monitoring forearm gauntlet 501, 503, oriented in a predetermined upper limb position. The gauntlets 501, 503 are each oriented on and encompassing the user's forearms. The exact position of the gauntlets 501, 503 on the user's forearms may vary due to variations in the gauntlets 501, 503 and the user's forearm size and shape. In the depicted predetermined upper limb position, the user's upper limbs 522 are oriented such that the user's palms are facing the opposing gauntlet and the user's fingers are wrapped around the opposing gauntlet. In this orientation, the user's upper limbs 522 are not effectively able to 1) steer a vehicle and/or 2) to operate the vehicle's ancillary controls. The forearm gauntlets 501, 503 may be equipped with a variety of features as described above with regard to FIG. 1.

In an example implementation, the gauntlets 501, 503 may be oriented in an unlocked (or non-compliant) orientation and a locked (or compliant) orientation. The locked (or compliant) orientation is depicted in FIG. 5. In the unlocked orientation, the user has a gauntlet secured to each of the user's forearms. When placed in the locked orientation, the user places his/her forearms together with each of his/her palms facing an opposing gauntlet. In one implementation, biomonitors in one or both of the gauntlets (see e.g., biomonitor 208 of FIG. 2) may monitor temperature, pulse, and/or pressure to ensure that the user maintains his palms and/or fingers over the appropriate places on the opposing gauntlet. Each of the gauntlets 501, 503 may be equipped with a locking mechanism positioned on the inside of the user's forearms that is configured to interface with the opposing gauntlet.

Figure 6:
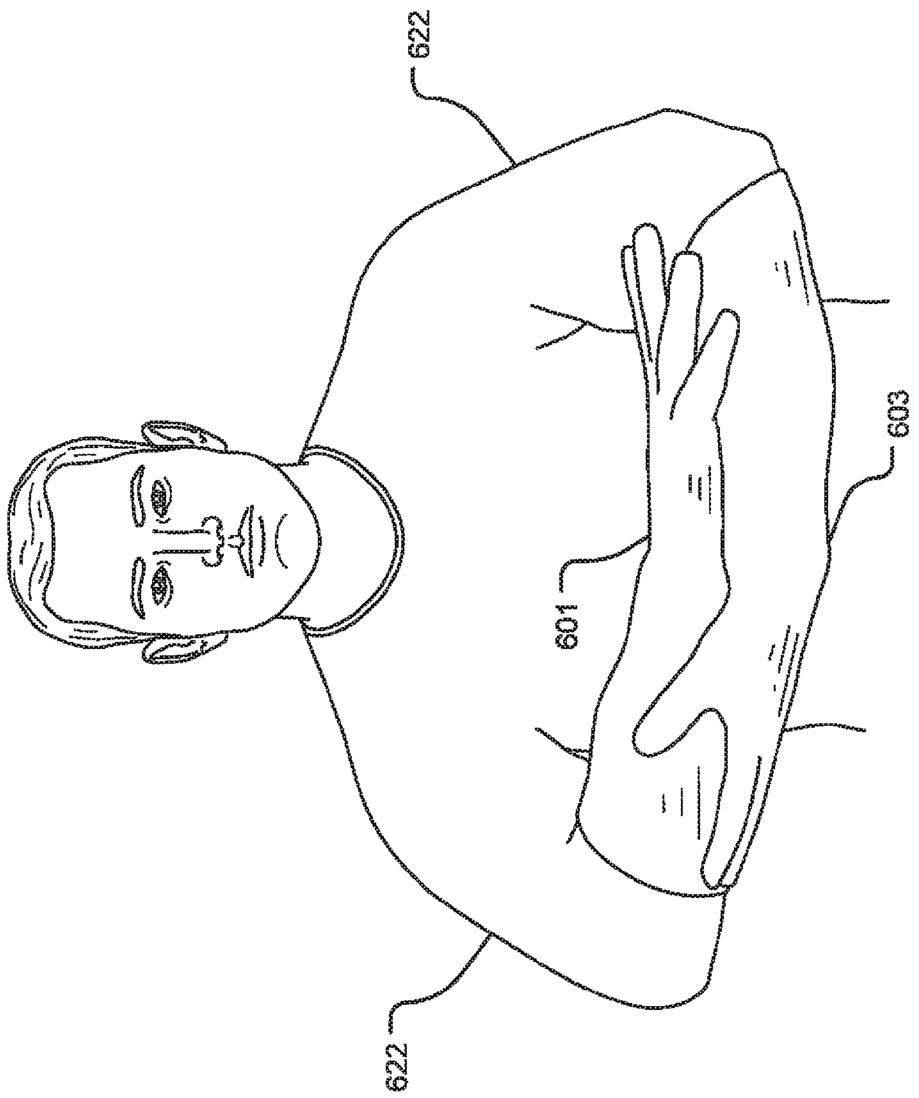
FIG. 6 illustrates a user's upper limbs, each equipped with an example position monitoring fingered forearm gauntlet, oriented in a predetermined upper limb position.

FIG. 6 illustrates a user's upper limbs 622, each equipped with an example position monitoring fingered forearm gauntlet 601, 603, oriented in a predetermined upper limb position. The gauntlets 601, 603 are each oriented on and encompassing at least a portion of the user's forearms, wrists, hands, and fingers. The exact position of the gauntlets 601, 603 on the user's upper limbs 622 may vary due to variations in the gauntlets 601, 603 and the user's upper limbs 622 size and shape. In the depicted predetermined upper limb position, the user's upper limbs 622 are oriented such that the user's palms are facing the opposing gauntlet and the user's fingers are wrapped around the opposing gauntlet. In this orientation, the user's upper limbs 622 are not effectively able to 1) steer a vehicle and/or 2) to operate the vehicle's ancillary controls. The gauntlets 601, 603 may be equipped with a variety of features as described above with regard to FIG. 1.

In an example implementation, the gauntlets 601, 603 may be oriented in an unlocked (or non-compliant) orientation and a locked (or compliant) orientation. The locked (or compliant) orientation is depicted in FIG. 6. In the unlocked orientation, the user has a gauntlet secured to at least a portion of the user's forearms, wrists, hands, and fingers. When placed in the locked orientation, the user places his/her forearms together with each of his/her palms facing an opposing gauntlet. In one implementation, biomonitors in one or both of the gauntlets (see e.g., biomonitor 308 of FIG. 3) may monitor temperature, pulse, and/or pressure to ensure that the user maintains his palms and/or fingers within the opposing gauntlet. Each of the gauntlets 601, 603 may be equipped with a locking mechanism positioned on the inside of the user's forearms that is configured to interface with the opposing gauntlet. Further, the finger and/or hand portions of the gauntlets 601, 603 may be retractable under certain circumstances to allow the user better use of his/her hands when the user is not required to maintain his/her upper arms in a compliant position.

Figure 7:
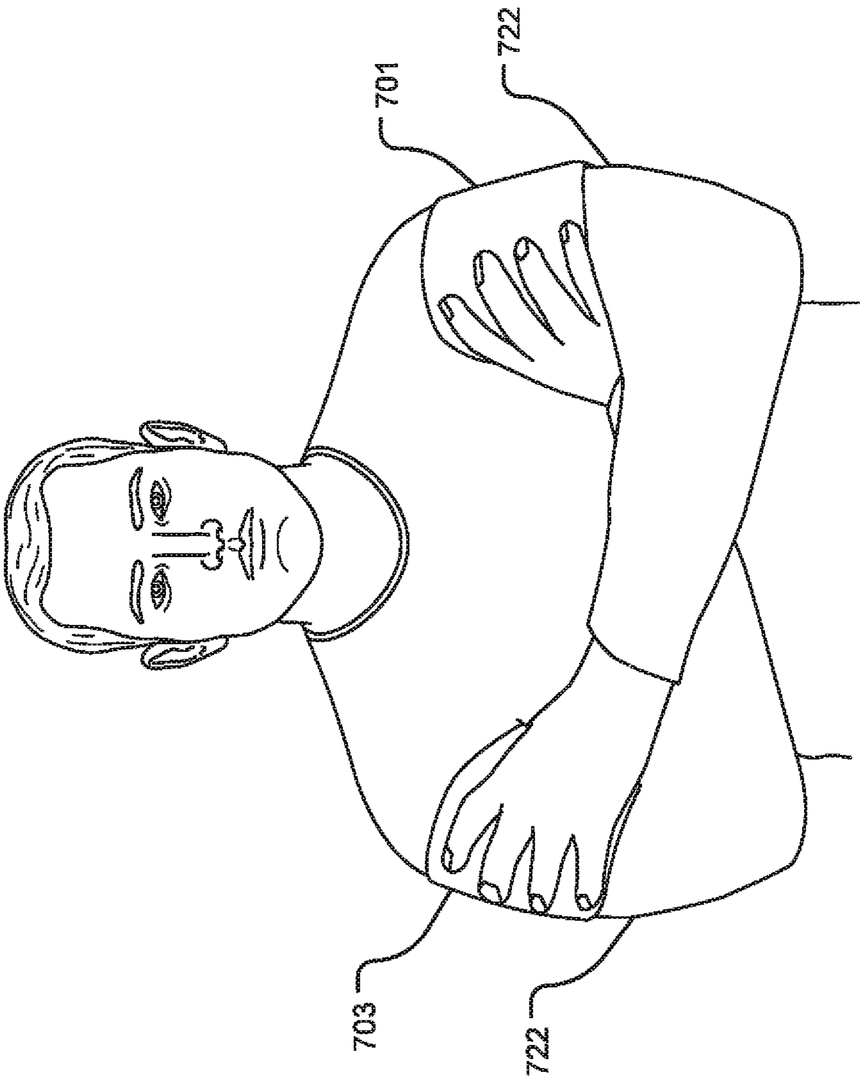
FIG. 7 illustrates a user's upper limbs, each equipped with an example position monitoring arm cuff, oriented in a predetermined upper limb position.

FIG. 7 illustrates a user's upper limbs 722, each equipped with an example position monitoring arm cuff 701, 703, oriented in a predetermined upper limb position. The cuffs 701, 703 are each oriented on the user's upper arms in the vicinity of the user's biceps and triceps. The exact position of the cuffs 701, 703 on the user's upper arms may vary due to variations in the cuffs 701, 703 and the user's upper arm size and shape. In the depicted predetermined upper limb position, the user's upper limbs 722 are oriented such that the user's hand and fingers are grasping the opposing arm cuff. In this orientation, the user's upper limbs 722 are not effectively able to 1) steer a vehicle and/or 2) to operate the vehicle's ancillary controls. The cuffs 701, 703 may be equipped with a variety of features as described above with regard to FIG. 1.

In an example implementation, the cuffs 701, 703 may be oriented in an unlocked (or non-compliant) orientation and a locked (or compliant) orientation. The locked (or compliant) orientation is depicted in FIG. 7. In the unlocked orientation, the user has a cuff secured to each of the user's upper arms. When placed in the locked orientation, the user places his/her hands against the opposing cuff with his/her fingers grasping the opposing cuff. In one implementation, biomonitors in one or both of the cuffs 701, 703 (see e.g., biomonitor 208 of FIG. 2) may monitor temperature, pulse, and/or pressure to ensure that the user maintains his palms and/or fingers over the appropriate places on the opposing cuff. In yet another implementation, the cuffs 701, 703 are located over the user's elbow area rather than or in addition to over the user's biceps and triceps.

Figure 8:
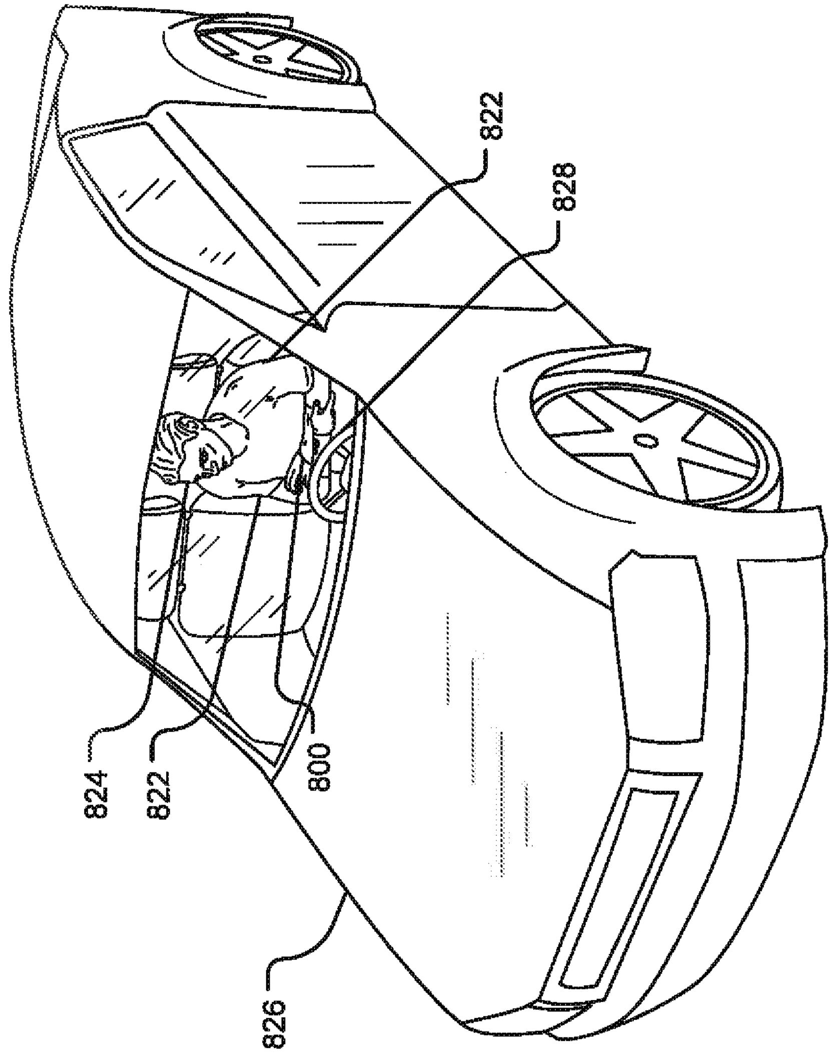
FIG. 8 illustrates a user seated in a vehicle with the user's upper limbs oriented in an example predetermined upper limb position.

FIG. 8 illustrates a user 824 seated in a vehicle 826 with the user's upper limbs 822 oriented in an example predetermined upper limb position. The user 824 is sitting in the driver's seat of the vehicle 826. So long as the user 824 is required to maintain his/her upper limbs 822 in the depicted predetermined upper limb position, the user 824 is unable to move his/her upper limbs 822 in a way that effectively operates a steering wheel 828 of other ancillary controls of the vehicle 826. This effectively prevents the user 824 from operating the vehicle 826.

In one implementation, as long as the vehicle 826 is a rest or moving very slowly (i.e., a speed of less than 10 mph), the user 824 may not be required to maintain his/her upper limbs 822 in the predetermined upper limb position. However, once the speed of the user 824 (as monitored by gauntlets 800) exceeds 10 mph, the user 824 is required to orient his/her upper limbs 822 in the predetermined upper limb position and is no longer able to effectively operate the vehicle 826. If the user 824 is a passenger of the vehicle 826, the user 824 is still required to orient his/her upper limbs 822 in the predetermined upper limb position, but the user 824 can effectively be a passenger in the vehicle 826 with his/her upper limbs 822 in the predetermined upper limb position.

While the present application discusses both cuffs and gauntlets for securing and monitoring a user's upper limb position, cuffs as contemplated herein encompass both cuff and gauntlet implementations of the presently disclosed technology.

Figure 9:
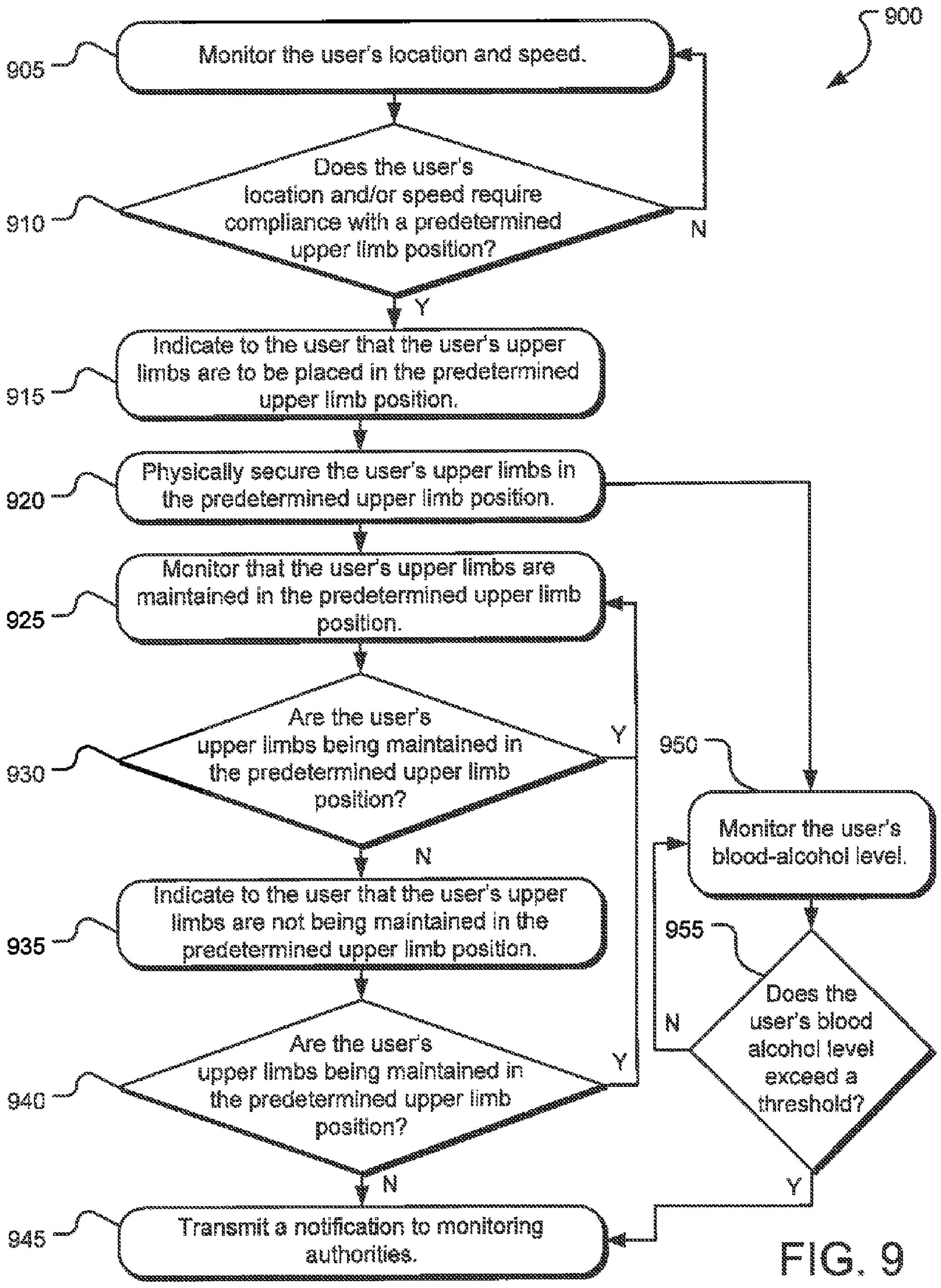
FIG. 9 illustrates example operations for restricting a user's operation of a vehicle using upper limb position monitoring cuffs.

FIG. 9 illustrates example operations 900 for restricting a user's operation of a vehicle using upper limb position monitoring cuffs. Not all operations 900 are required for all implementations of the presently disclosed technology.

A monitoring operation 905 monitors the user's location and speed. The user wears the compliance monitoring cuffs on his/her upper limbs. In one implementation, the cuffs are equipped with a geolocating device that provides the position and speed information. A decision operation 910 determines if the user's location and/or speed require compliance with a predetermined upper limb position. For example, compliance with the predetermined upper limb position may only be required when the user's speed is greater than 10 miles per hour and less than 150 miles per hour. As a result, the user is not required to maintain the predetermined upper limb position when the user is walking and riding on a commercial airplane. Other thresholds and ranges for the user's speed are contemplated herein. Further, the predetermined upper limb position may only be active is certain locations. For example, the user may only be required to maintain the predetermined upper limb position within the United States for legal or logistical reasons. The predetermined upper limb position places the user's upper limbs in a position that renders them ineffective at operating a vehicle. Various implementations of the predetermined upper limb position are depicted in FIGS. 4-7 and related description.

If the user's speed and/or location do not require compliance with the predetermined upper arm position, monitoring operation 905 repeats. If the user's speed and/or location do require compliance with the predetermined upper arm position, indicating operation 915 indicates to the user that the user's upper limbs are to be placed in the predetermined upper limb position. Indicating operation 915 may be accomplished through one or more of a sound, light, and tactile vibration, for example. Further, securing operation 920 may physically secure the user's upper limbs in the predetermined upper limb position. Securing operation 920 may be accomplished through a latching mechanism or magnetic or electronic clasp, for example.

A monitoring operation 925 monitors that the user's upper limbs are maintained in the predetermined upper limb position. The monitoring operation 925 may be accomplished using one or more of a proximity sensor, contact sensor, and biometric readings, for example. A decision operation 930 determines if the user's upper limbs are being maintained in the predetermined upper limb position. If so, monitoring operation 925 repeats. If not, an indicating operation 935 indicates to the user that the user's upper limbs are not being maintained in the predetermined upper limb position. Indicating operation 935 may be accomplished through one or more of a sound, light, and tactile vibration, for example.

A decision operation 940 determines if the user's upper limbs are being maintained in the predetermined upper limb position. If so, monitoring operation 925 repeats. If not, a transmitting operation 945 transmits a notification to monitoring authorities. The notification may be used to track the user's compliance with the predetermined arm position for probation purposes, for example. Further, if the user continues to fails to comply with the predetermined arm position, authorities may be dispatched to locate and arrest the user.

Further, a monitoring operation 950 may monitor the user's blood-alcohol level, among other things. A decision operation 955 determines if the user's blood alcohol level exceeds a threshold. If not, monitoring operation 950 repeats. If so, the transmitting operation 945 transmits a notification to the monitoring authorities.

The embodiments of the invention described herein are implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A system for detecting compliance by a user in maintaining a predetermined upper limb position, the system comprising:

an upper limb cuff configured to removably couple to an upper limb of the user;

an opposing upper limb cuff configured to removably couple to an opposing upper limb of the user;

a first compliance monitor coupled to the upper limb cuff;

a second compliance monitor coupled to the opposing upper limb cuff, the first and second compliance monitors each having one or more sensors configured to detect a proximity between the first compliance monitor and the second compliance monitor, the detectable proximity when the upper limb of the user is in a first orientation and the opposing limb of the user is in a second orientation, the first orientation and the second orientation collectively positioning the upper limb and the opposing upper limb in the predetermined upper limb position; and a geolocator configured to determine a speed of the user, the upper limb cuff including a male component of a latch mechanism and the opposing upper limb cuff including a female component of the latch mechanism, the male component configured to engage the female component when the speed of the user exceeds a predefined speed.

2. The system of claim 1, wherein the first orientation and the second orientation are substantially opposite directions.

3. The system of claim 1, wherein the proximity is less than 0.5 inches in the predetermined upper limb position.

4. A system for detecting compliance by a user in maintaining a predetermined upper limb position, the system comprising:

an upper limb cuff configured to removably couple to an upper limb of the user;

an opposing upper limb cuff configured to removably couple to an opposing upper limb of the user;

a first compliance monitor coupled to the upper limb cuff;

a second compliance monitor coupled to the opposing upper limb cuff, the first and second compliance monitors each having one or more sensors configured to detect an angle of a first orientation of the upper limb relative to a second orientation of the opposing upper limb, the angle associated with the predetermined upper limb position between the first orientation and the second orientation; and a geolocator configured to determine a speed of the user, the upper limb cuff including a male component of a latch mechanism and the opposing upper limb cuff including a female component of the latch mechanism, the male component configured to engage the female component when the speed of the user exceeds a predefined speed.

5. The system of claim 4, wherein the angle is between 5 and 180 degrees in the predetermined upper limb position.

6. The system of claim 4, wherein the male component is a triangular protrusion and the female component is a matching recess.

7. The system of claim 4, wherein the male component is a tab and the female component is a slot.

8. The system of claim 1, wherein the first orientation is substantially parallel to the second orientation, such that the predetermined upper limb position places a forearm of the upper limb substantially parallel to an opposing forearm of the opposing upper limb with a hand of the upper limb facing towards an elbow of the opposing upper limb.

9. The system of claim 8, wherein a wrist of the upper limb is positioned next to an opposing wrist of the opposing upper limb.

10. The system of claim 9, wherein an inside of the wrist of the upper limb is facing an inside of the opposing wrist of the opposing upper limb.

11. The system of claim 8, wherein a wrist of the upper limb is positioned next to the opposing forearm.

12. The system of claim 11, wherein an inside of the wrist of the upper limb is facing the opposing forearm.

13. The system of claim 1, wherein the first orientation is angled relative to the second orientation, such that the predetermined upper limb position places a forearm of the upper limb along a first line and an opposing forearm of the opposing upper limb along a second line that intersects the first line.

14. The system of claim 13, wherein a hand of the upper limb is facing towards an upper arm of the opposing upper limb.

15. The system of claim 14, wherein a palm of the hand is positioned next to the upper arm.

16. A system for detecting compliance by a user in maintaining a predetermined upper limb position, the system comprising:

an upper limb cuff configured to removably couple to an upper limb of the user;

an opposing upper limb cuff configured to removably couple to an opposing upper limb of the user;

a first compliance monitor coupled to the upper limb cuff; and a second compliance monitor coupled to the opposing upper limb cuff, the first and second compliance monitors each having one or more sensors configured to detect a proximity between the first compliance monitor and the second compliance monitor, the detectable proximity when the upper limb of the user is in a first orientation and the opposing limb of the user is in a second orientation, the first orientation and the second orientation collectively positioning the upper limb and the opposing upper limb in the predetermined upper limb position;

a compliance indicator configured to provide an indication of the predetermined upper limb position; and a transmitter configured to send information regarding the predetermined upper limb position to a recipient.

17. The system of claim 16, wherein the recipient is a monitoring authority.

18. The system of claim 16, wherein the recipient is a portable computing device.

19. The system of claim 16, further comprising:

a biomonitor configured to monitor at least one of: vital signs of the user; a temperature of the user; a pulse of the user; a blood pressure of the user; or a blood-alcohol level of the user.

20. The system of claim 16, further comprising:

a geolocator in communication with the compliance monitor, the geolocator configured to track a speed of the user, the compliance monitor detecting the compliance of the user with the predetermined upper limb position only when the speed of the user exceeds a threshold.

21. A method for directing compliance by a user in maintaining a predetermined upper limb position, the method comprising:

monitoring a speed of the user;

providing an indication to the user when the speed exceeds a threshold, the indication informing the user of a requirement to comply with the predetermined upper limb position where an upper limb of the user in an upper limb cuff and an opposing upper limb in an opposing upper limb cuff are collectively positioned in the predetermined upper limb position; and detecting a proximity of the upper limb cuff to the opposing upper limb cuff to detect the predetermined upper limb position using a compliance monitor.

22. The method of claim 21, further comprising:

transmitting information regarding the predetermined upper limb position to a recipient.

* * * * *